(12) United States Patent
Griffith et al.

(10) Patent No.: US 6,325,764 B1
(45) Date of Patent: *Dec. 4, 2001

(54) BI-LEVEL CHARGE PULSE APPARATUS TO FACILITATE NERVE LOCATION DURING PERIPHERAL NERVE BLOCK PROCEDURES

(75) Inventors: Richard Lee Griffith, Allendale; Robert J. Strowe, Ramsey, both of NJ (US); Jonathan C. Newell, Glenmont; Peter M. Edic, Albany, both of NY (US); Ralph F. Messina, Belleville; Frederick Charles Houghton, Sussex, both of NJ (US)

(73) Assignee: Becton, Dickinson and Company, Franklin Lakes, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/967,054

(22) Filed: Nov. 10, 1997

Related U.S. Application Data

(63) Continuation-in-part of application No. 08/695,151, filed on Aug. 5, 1996, now Pat. No. 5,853,373.

(51) Int. Cl.[7] ....................................................... A61B 5/05
(52) U.S. Cl. ............................................ 600/554; 607/116
(58) Field of Search ................................. 600/546, 554, 600/373, 548; 606/36, 44; 607/116

(56) References Cited

U.S. PATENT DOCUMENTS 3,682,162 * 8/1972 Colyer .................................. 600/554

4,515,168 * 5/1985 Chester et al. ....................... 600/554

(List continued on next page.)

FOREIGN PATENT DOCUMENTS 26 52 050 A1    5/1978  (DE) .

OTHER PUBLICATIONS

P. P. Raj, et al: Infraclavicular Brachial Plexus Block—A new Approach Anesthesia and Analgesia Current Reasearches 52:897–903, 1973.

(List continued on next page.)

*Primary Examiner*—Francis J. Jaworski
(74) *Attorney, Agent, or Firm*—Eric M. Lee

(57) ABSTRACT

A self-contained electrolocation apparatus of the present invention includes an electrically conducting needle cannula having a proximal end, a distal end and a hollow bore therethrough. The invention further includes a non-conductive tube having a proximal end and a distal end, the tube being mounted over the needle cannula so that the distal end of the non-conductive tube is proximal to the distal end of the needle cannula. The non-conductive tube has a conductive layer thereon, whereby the needle cannula and the conductive layer respectively define first and second conductors coaxially spaced from one another by the non-conductive tube. There is a grip fixedly attached to the needle cannula for manipulating the apparatus. The grip has an electrical stimulus generator circuit within it that is electrically connected to the first conductor and the second conductor. The stimulus generator circuit is capable of applying a potential across the conductors so that when the needle is positioned in a patient's tissue and the electrical stimulus generator circuit is activated, the potential is sufficient to induce a preselected current thereby providing a charge pulse between the distal end of the conductive layer and the distal end of said needle cannula through the patient's tissue. The charge pulse is sufficient to induce a twitch response in the patient.

48 Claims, 13 Drawing Sheets

U.S. PATENT DOCUMENTS

| | | | | |
|---|---|---|---|---|
| 4,563,570 | * | 1/1986 | Johns | 219/240 |
| 4,616,660 | * | 10/1986 | Johns | 600/554 |
| 4,962,766 | * | 10/1990 | Herzon | 600/554 |
| 5,046,506 | * | 9/1991 | Singer | 600/554 |
| 5,273,525 | * | 12/1993 | Hofmann | 607/116 |
| 5,284,154 | * | 2/1994 | Raymond et al. | 600/554 |
| 5,562,718 | * | 10/1996 | Palermo | 607/46 |
| 5,779,642 | * | 7/1998 | Nightengale | 600/461 |
| 5,853,373 | * | 12/1998 | Griffith et al. | 600/554 |

OTHER PUBLICATIONS

W. F. Ganong: Physiology of Nerve and Muscle Cells Review of Medical Physiology (Lange Medical Publications) 18–31, 1977.

D. Selander, et al: Peripheral Nerve Injury due to Injection Needles used for Regional Anesthesia Acta Anaesth. Scand. 21:182–8, 1977.

D. Selander, et al: Paresthesiae or no Paresthesiae? Acta Anaesth. Scand. 23:27–33, 1979.

C. E. Pither, et al: Peripheral Nerve Stimulation with Insulated and Uninsulated Needles Efficacy and Characteristics (abstract) Regional Anesthesia 9:42–3, 1984.

G. Bashein, et al: Electrical Nerve Location: Numerical and Electrophoretic Comparison of Insulated vs Uninsulated Needles Anesth Analg 63:919–24, 1984.

G. Bashein, et al: Electrolocation: Insulated versus Non–insulated Needles Reg. Anesth. 9:31, 1984.

D. J. Ford, et al: Comparison of Insulated and Uninsulated Needles for Locating Peripheral Nerves with a Peripheral Nerve Stimulator Anesth Analg 63:925–8, 1984.

C. E. Pither, et al: The Use of Peripheral Nerve Stimulators for Regional Anesthesia: A Review of Experimental Characteristics, Technique, and Clinical Applications Regional Anesthesia 10:49–58, 1985.

J. A. W. Wilsmith and E. N. Armitage: The Management of Regional Anesthesia Principles and Practice of Regional Anesthesia Principles and Practice of Rgional Anaesthesia (Churchill Livingston) 45–9, 1987.

D. A. McClain, et al: Interscalene Approach to the Brachial Plexus: Paresthesiae versus Nerve Stimulator Regional Anesthesia 12:80–3, 1987.

W. G. Horton: Use of Peripheral Nerve Stimulator Problems in Anesthesia 1:588–91, 1987.

R. E. Brown, et al: Continuous Peripheral Nerve Infusion of Local Anesthetic for Management of Pain due to Reflex Sympathetic Dystrophy Regional Anesthesia 15(Suppl 1):88, 1990.

A. P. Baranowski and C. E. Pither: A Comparison of Three Methods of Axillary Brachial Plexus Anaesthesia Anaesthesia 45:362–5, 1990.

P. P. Raj (ed.): Monitoring and Equipment for Regional Anesthesia Clinical Practice of Regional Anesthesia (Churchill Livingston) 61–5, 161–9, 1991.

R. P. Jones, et al: Voltage Fields Surrounding Needles Used in Regional Anaesthesia British Journal of Anaesthesia 68:515–8, 1992.

A. Tulchinsky, et al: Needle Polarity Causes Three–fold Difference in Threshold Current During Axillary Block Anesthesiology (ASA Abstracts) 77,A873, 1992.

F. X. Reigler: Brachial Plexus Block with the Nerve Stimulator: Motor Response Characteristics at Three Sites Regional Anesthesia 17:295–9, 1992.

D. L. Brown: Local Anesthetics and Regional Anesthesia Equipment Atlas of Regional Anesthesia (W. B. Saunders) 7–11, 1992.

A. S. C. Rice and S. B. McMahon: Peripheral Nerve Injury Caused by Injection Needles Used in Regional Anaesthesia: Influence of Bevel Configuration, Studied in a Rat Model Br. J Anaesth 69:433–8, 1992.

R. S. Purdham: Current Regional Anesthesia Techniques of the Brachial Plexus: 1992 CRNA 3:154–63, 1992.

J. Lavoie, et al: Axillary Plexus Block Using a peripheral Nerve Stimulator: Single or Multiple Injections Can J. Anaesth 39:583–6, 1992.

A. Tulchinsky, et al: Nerve Stimulator Polarity and Brachial Plexus Block Anesthe Analg 77:100–3, 1993.

D. Fletcher, et al: Addition of Fentanyl to 1.5% Lidocaine Does Not Increase the Success of Axillary Plexus Block Regional Anesthesia 19:183–8, 1994.

M. K. Urban and B. Urquhart: Evaluation of Brachial Plexus Anesthesia for Upper Extremity Surgery Regional Anesthesia 19:175–82, 1994.

S. Karpal, et al: Ultrasound–guided Supraclavicular Approach for Regional Anesthesia of the Brachial Plexus Anesth Analg 78:507–13, 1994.

* cited by examiner

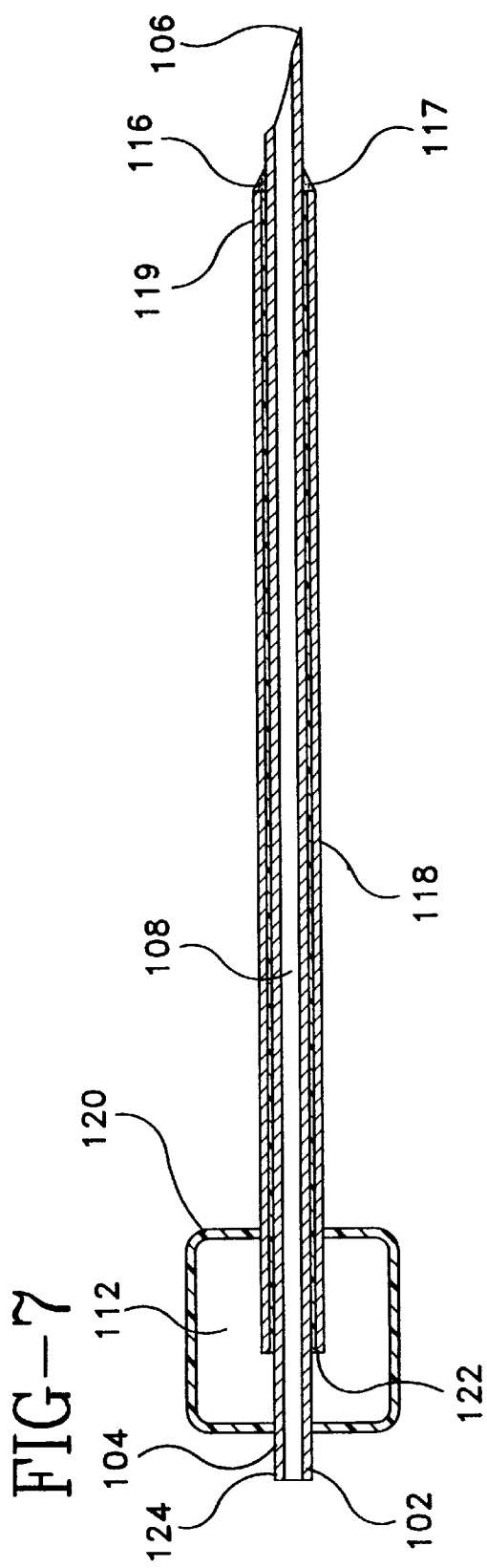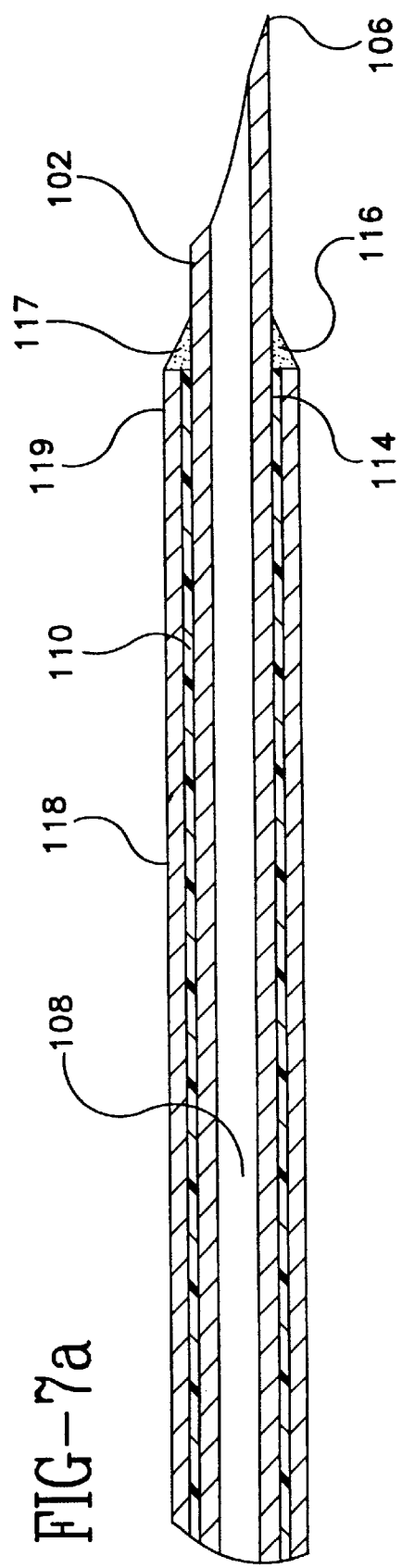

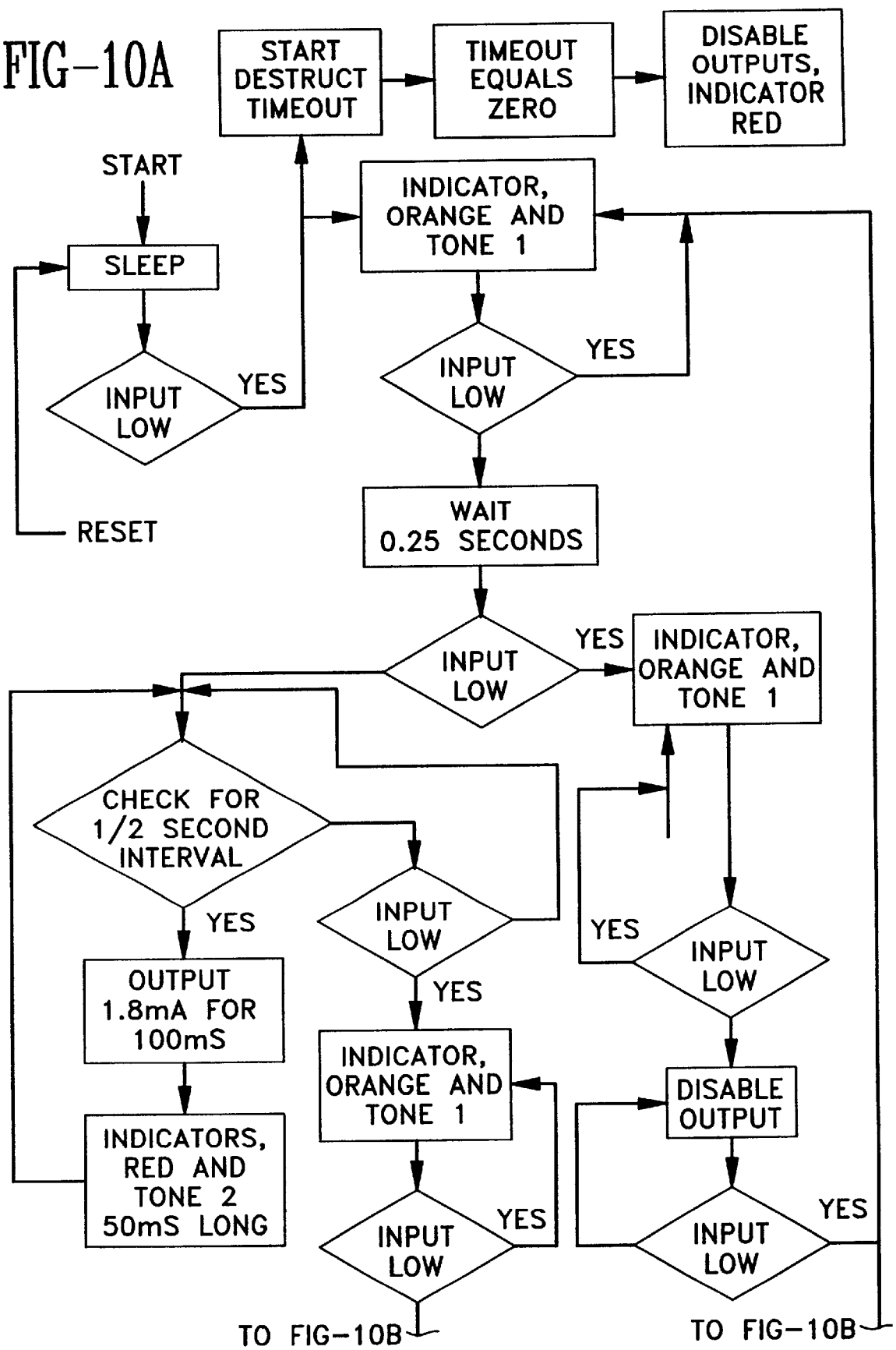

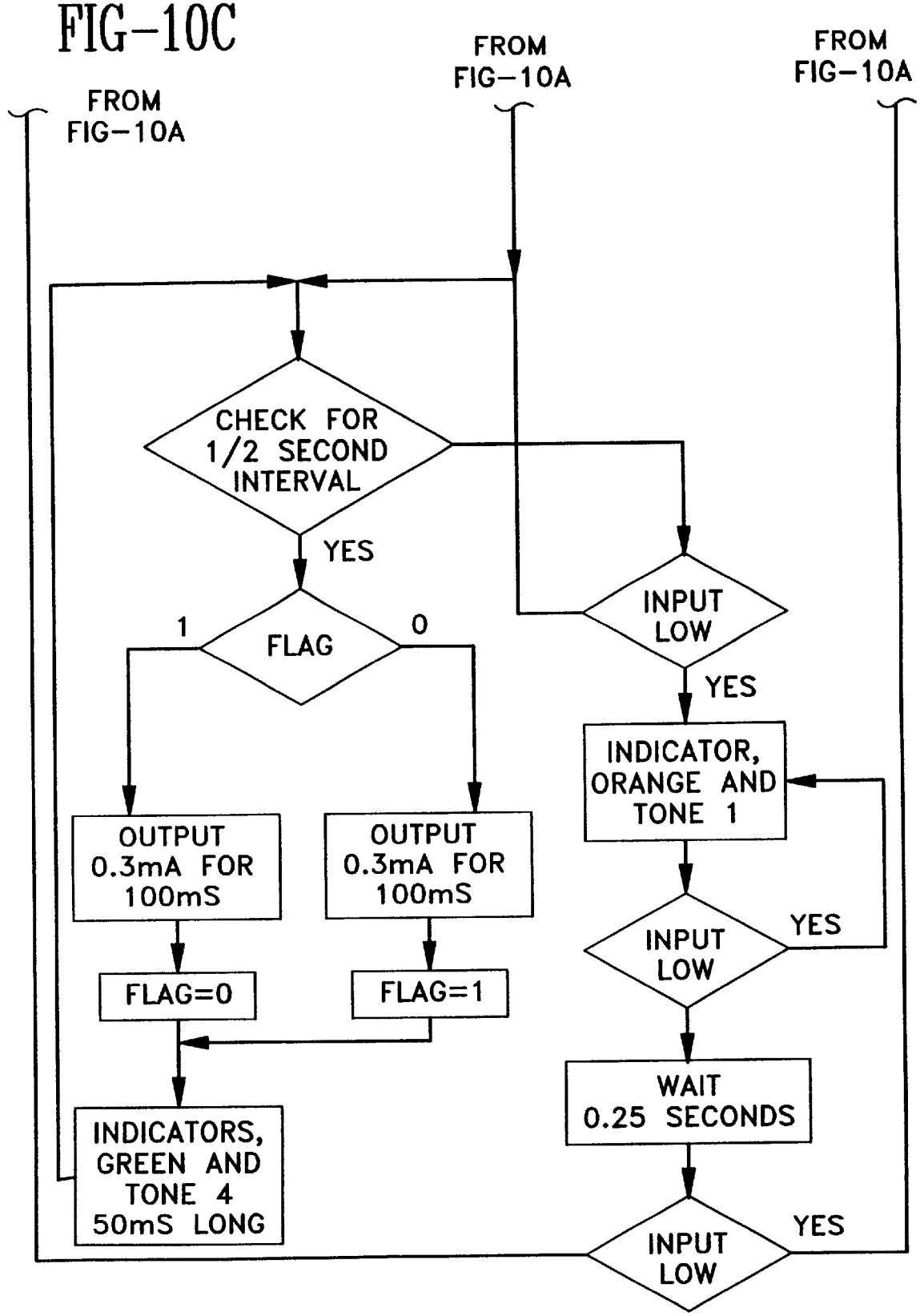

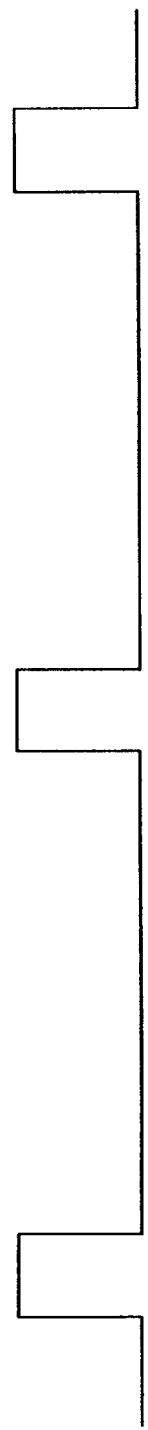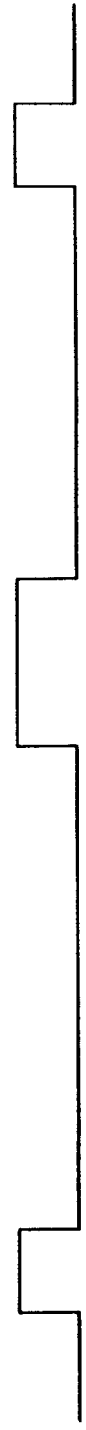
FIG-11A
FIG-11B
FIG-11C

BI-LEVEL CHARGE PULSE APPARATUS TO FACILITATE NERVE LOCATION DURING PERIPHERAL NERVE BLOCK PROCEDURES

This application is a continuation-in-part of U.S. Application Ser. No. 08/695,151, filed on Jul. 5, 1996, now U.S. Pat. No. 5,853,333.

BACKGROUND OF THE INVENTION

1. Field of the Invention

The subject invention relates to an apparatus for efficiently locating a nerve and for subsequently delivering an anesthetic to the nerve.

2. Description of the Prior Art

Many medical procedures require a patient to be at least locally anesthetized. A regional anesthesia or nerve block offers advantages over general anesthesia for many medical procedures. For example, a regional anesthesia or nerve block typically is less traumatic to the patient undergoing surgery and often permits a shorter post-operative recovery.

A regional anesthesia or nerve block necessarily requires location of the nerve to which anesthetic agent will be administered. The prior art includes methods for locating the nerve. In most such prior art methods, the doctor typically uses general knowledge of physical anatomy to approximately locate the targeted nerve. In accordance with one prior art method, an electrically conductive pad is positioned on the skin on a portion of the patient's body at some distance from the targeted nerve. For example, if the targeted nerve is in the shoulder, the electrically conductive pad may be secured to a distal portion of the arm. The electrically conductive pad is connected by a wire to a prior art stimulator box that is capable of generating electrical current, as explained further herein. An electrically insulated needle cannula with an uninsulated conductive tip is then urged through the skin and subcutaneous tissue in the general direction of the nerve to be anesthetized. The prior art needle is connected by a wire to the prior art electrical stimulator box.

The prior art stimulator box is electrically powered and is operative to produce an adjustable current pulse for a duration of approximately 100–200 microseconds ("$\mu S$"). The current pulse is set initially to a level of approximately 1.0–5.0 milliamps ("mA"). This current level typically is sufficient to stimulate the targeted nerve when the needle has been placed into the tissue in the approximate area of the targeted nerve. The stimulation will cause a noticeable muscle twitch on areas of the body controlled by the targeted nerve (e.g., the fingers). The current then is decreased slowly until the twitching disappears. The prior art needle then is advanced slowly toward the targeted nerve until the twitching reappears. This iterative procedure continues until the prior art needle is able to generate noticeable muscle twitches at a current level of approximately 0.2–0.3 milliamps. At this point, the prior art needle is considered to be sufficiently close to the targeted nerve for administration of the anesthetic agent. The anesthetic agent then is delivered directly through the needle while the needle continues to produce the current pulses. Cessation of the muscle twitch typically is considered to indicate successful location of the nerve.

The prior art electrolocation procedure is intended to ensure accurate placement of a needle for delivery of anesthetic. However, the prior art device and the prior art procedure for electrolocation of a targeted nerve have several drawbacks. For example, the prior art electrolocation device, including the stimulator box, is a fairly large, costly and reusable piece of equipment that is not easily sterilized. Thus, there are problems with using the prior art electrolocation device in the sterile environment of an operating room. It is typically necessary to employ two technicians for carrying out this prior art procedure, namely a first technician operating under sterile conditions and manipulating the needle, and a second technician spaced from the first technician and operating under non-sterile conditions to incrementally decrease the current level. The use of two technicians necessarily requires fairly high costs and requires considerable coordination and communication between the two technicians.

Second, the prior art electrolocation device does not provide a definitive indication of when the needle is properly positioned for injecting the anesthetic. The attending physician must rely upon judgment and experience to determine when the needle is in the optimum position.

Third, the considerable distance between the insulated needle and the prior art conductive pad requires the generation of a relatively high voltage to achieve the desired current level. A voltage of at least 25 volts ("V") is common in the prior art electrolocation apparatus. These relatively high voltage levels limit the use of the prior art apparatus. For example, the high voltage levels can affect the performance of pacemakers and other implanted electronic devices. Hence, the prior art electrolocation device generally cannot be used on patients with implanted electronics.

Additionally, the relatively high energy creates the risk of arcing. Hence the prior art electrolocation apparatus cannot be employed in many surgical environments, such as those where oxygen is being used, due to the risk of fire or explosion. The high current levels may also create the potential for tissue damage in proximity to the needle.

SUMMARY OF THE INVENTION

A self-contained electrolocation apparatus of the present invention includes an electrically conducting needle cannula having a proximal end and a distal end. The invention further includes a non-conductive tube having a proximal end, a distal end and an open passageway therethrough, the tube being mounted over the needle cannula so that the distal end of the non-conductive tube is proximal to the distal end of the needle cannula. The non-conductive tube has a conductive layer that has a distal end thereon, whereby the needle cannula and the conductive layer respectively define first and second conductors coaxially spaced from one another by the non-conductive tube. There is a grip fixedly attached to the needle cannula for manipulating the apparatus. The grip has an electrical stimulus generator circuit within it that is electrically connected to the first conductor and the second conductor. The stimulus generator circuit is capable of applying a potential across the conductors so that when the needle cannula is positioned in a patient's tissue and the electrical stimulus generator circuit is activated, the potential is sufficient to induce a preselected current thereby providing a charge pulse between the distal end of the conductive layer and the distal end of said needle cannula through the patient's tissue. The charge pulse is sufficient to induce a twitch response in the patient.

As noted above, the voltage required for an electrolocation apparatus is a function of the distance between two conductors and the contact resistance to the patient. To substantially minimize the distance, the subject invention provides both conductors on the needle cannula. More particularly, the electrolocation apparatus of the subject invention may employ a needle assembly having a pair of coaxially disposed conductors. An inner conductor of the pair of coaxial conductors may be defined by the needle. A non-conductive sheath or tube may then be mounted over the inner conductor and may be plated, coated, coextruded or otherwise provided with an electrically conductive material, which functions as the outer conductor. A bevel or chamfer may be defined at the distal end of the non-conductive tube. The bevel may be defined by a non-conductive adhesive at the distal end of the tube. The beveled adhesive functions to hold the tube in place and also facilitates entry of the needle assembly into the patient. The spacing between the conductors of the electrolocation device is defined by the distance from the distal edge of the bevel to the conductive sheath, which preferably is slightly more than 1.0 millimeter ("mnm"). In view of this very small distance, a very low voltage can be used to generate the required current. It is believed by the inventors herein that this aspect of the invention makes the subject electrolocation apparatus suitable for use with patients having implanted electronic devices, such as pacemakers. Furthermore, the low energy level permits the subject electrolocation apparatus to be used in virtually all operating room environments, including those where prior art electrolocation apparatus had created the potential for combustion. Additionally the low voltage permits simple electronic circuitry that can be provided conveniently in a small package.

As noted above, the prior art electrolocation device had required two technicians, namely a first technician to carefully manipulate the needle and a second technician to carefully vary the current level. The subject electrolocation apparatus employs entirely different structure that operates under entirely different principles, and enables use of the subject electrolocation apparatus by a single practitioner. The electrolocation apparatus takes advantage of the determination that the threshold electrical parameter for generating a muscle twitch is measured more accurately in terms of electrical charge rather than electrical current. Electrical charge is the product of current and time, and charge can be varied by changing either the current level or the time duration. In a first preferred embodiment, the subject electrolocation apparatus generates constant current pulses; however, the sequential pulses alternate between a relatively long duration and a relatively short duration. In this manner, sequential constant current pulses alternate between the relative high charge and a relatively low charge. In a second embodiment, the electrolocation apparatus is operative to alternately deliver relatively high current pulses (e.g., 0.5 mA) and relatively low current pulses (e.g., 0.1–0.2 mA). Each pulse may be of the same duration (e.g., 0.1–0.2 milliseconds ("mS")) and the pulses may be generated at uniform intervals (e.g., 0.25–2.0 seconds).

One approach to using the electrolocation device of the subject invention may include urging the needle into the patient and toward the targeted nerve. The relatively high charge pulses will generate muscle twitches at a location distant from the nerve after the skin has been penetrated (e.g., when the tip of the needle is about 1.0 cm from the targeted nerve). The relatively low charge pulses, however, will not produce a sufficient charge to generate muscle twitches at this initial distance. The pulses may be separated, for example, by approximately one-half second (hereafter, "½" or "0.5 " second(s)). Thus, the physician initially will observe muscle twitches at intervals of approximately one second, coinciding with the high charge pulses.

As the needle is moved toward the targeted nerve, the physician may observe a slight increase in the magnitude of the initially observed muscle twitches caused by the high charge pulses. Simultaneously, the physician will begin to observe small muscle twitches in response to the low charge pulse that follows each high charge pulse. Thus, using the preceding example, the physician will observe a large twitch in response to a high charge pulse followed 0.5 seconds later by a smaller twitch in response to a low charge pulse and then followed 0.5 seconds later by another larger twitch in response to a high charge pulse.

Twitches generated in response to the high charge pulses will quickly reach a peak, such that further movement of the needle toward the targeted nerve will not significantly increase the magnitude or severity of twitches resulting from high charge pulses.

Twitches generated in response to low charge pulses gradually will increase in magnitude and intensity as the needle continues to approach the targeted nerve. These changes in the magnitude and intensity of the low charge twitches will be readily observable by the physician inserting the needle. As the tip of the needle approaches the targeted nerve, the major and minor twitches will become substantially indistinguishable, and the physician will merely observe substantially identical muscle twitches at intervals of approximately 0.5 seconds or twice the interval initially observed. This will indicate to the physician that the tip of the needle is properly positioned for administration of the specified anesthetic. The anesthetic agent may then be urged through the needle and to the targeted nerve. The anesthetized nerve will then stop twitching, thereby giving the physician a clear indication that the targeted nerve has been reached and that the anesthetic has had its intended effect. The practitioner may then use the input device to switch the stimulation circuit to the quiescent mode and stop the charge pulses.

While principally described herein with the concept of generating sequentially alternating charge pulses of high and low levels, it will be appreciated by the skilled artisan that the construction of the electrolocation device and components described herein can be configured to produce a repeating pattern of graded charge pulses depending on the application desired. For instance, depending upon the anatomy of the region surrounding the nerve being sought, it may prove beneficial to have a repeating pattern of gradual decrease in charge pulse as the nerve is approached, rather than an alternating series of absolute high and low level charge pulses as the nerve is approached. That is to say, the apparatus and associated components can be configured such that rather than delivering an alternating series of high and low level charge pulses, it will deliver a repeating pattern of graded charge pulses, with the grade in each pattern declining from a selected maximum level charge pulse to a selected minimum level charge pulse. In this manner, for certain anatomies, the practitioner is provided with a greater range of clinical observations respective of nerve reaction to the charge pulses, thereby providing more accurate knowledge to the practitioner of the location of the apparatus to the nerve. Other patterns are also possible.

BRIEF DESCRIPTION OF THE DRAWINGS

FIG. 7 is a horizontal cross-sectional view of the electrolocation apparatus of FIG. 6 taken along the line 7—7;

FIG. 7a is a enlargement of the distal portion of the invention from the view of FIG. 7;

FIGS. 10a, 10b and 10c each are parts of a flow diagram describing the operation of the electrical stimulus generator circuit of FIG. 9;.

FIG. 11a is a schematic graphical representation of a first operating mode of the electrical stimulus generator circuit of FIG. 9;

FIG. 11b is a schematic graphical representation of a second operating mode of the electrical stimulus generator circuit of FIG. 9; and FIG. 11c is a schematic graphical representation of a third operating mode of the electrical stimulus generator circuit of FIG; 9.

DETAILED DESCRIPTION OF THE PREFERRED EMBODIMENT

Figure 1:
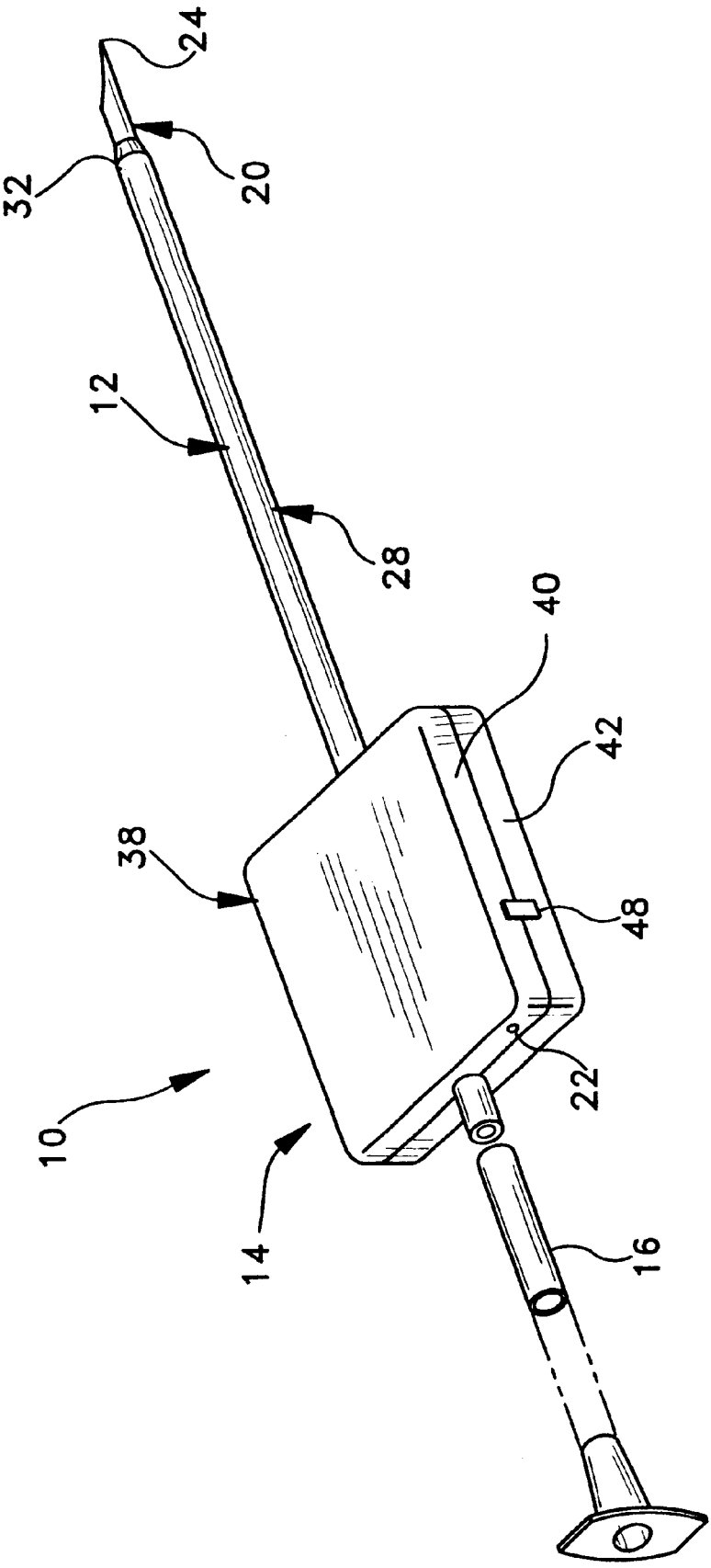
FIG. 1 is a perspective view of a bipolar electrolocation apparatus in accordance with the subject invention.

An electrolocation apparatus in accordance with the subject invention is identified generally by the numeral 10 in FIGS. 1. The apparatus 10 includes a needle assembly 12, a stimulator 14 and a tube 16 for delivering a dose of anesthetic through needle assembly 12.

Figure 2:
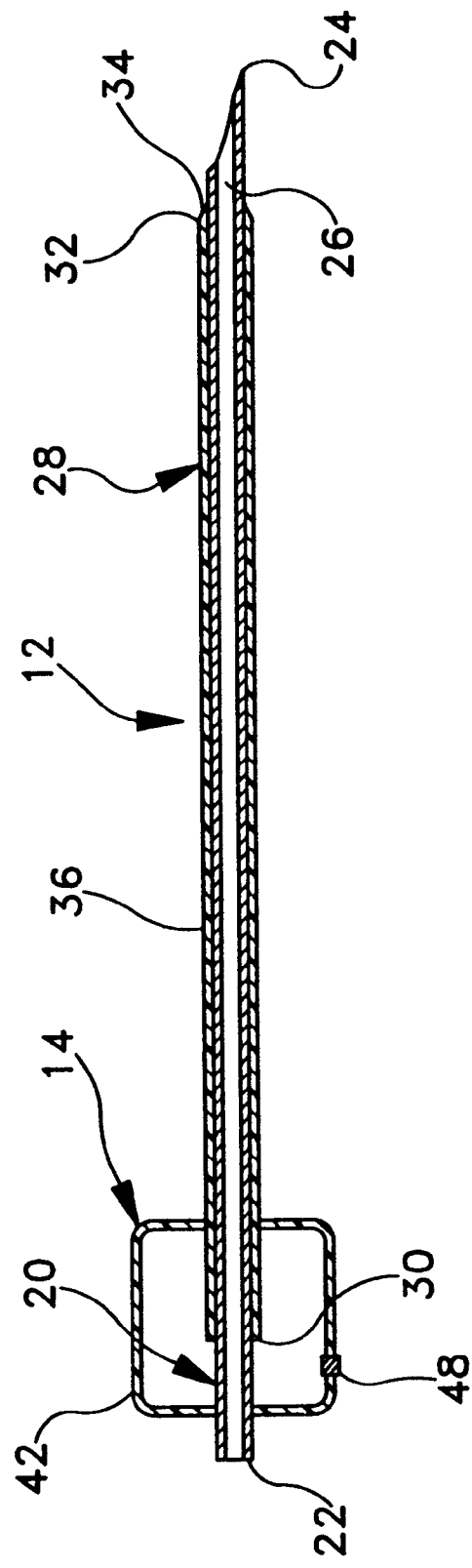
FIG. 2 is a cross-sectional view of a needle in accordance with the subject invention.

Needle assembly 12, as shown more clearly in FIG. 2, includes an elongate needle cannula 20 having opposed proximal and distal ends 22 and 24 and a lumen 26 extending continuously therebetween. Needle cannula 20 is formed from an electrically conductive material and preferably stainless steel. Proximal proportions of needle cannula 20 are securely mounted in stimulator 14 with proximal and distal ends of needle cannula 20 being on opposite sides of stimulator 14. Distal end 24 of needle cannula 20 is beveled to a point that facilitates piercing of tissue for accessing the targeted nerve.

Needle assembly 12 further includes a thin walled tube 28 coaxially disposed over needle cannula 20. Tube 28 has opposed proximal and distal ends 30 and 32 respectively, and is formed from a non-conductive material, such as polyimide. Proximal end 30 of tube 28 is disposed in stimulator 14 as explained further herein. Distal end 32 of tube 28 is spaced proximally from beveled distal end 24 of needle cannula 20. Tube 28 is dimensioned to be closely engaged against the outer cylindrical surface of needle cannula 20. However, secure retention of tube 28 on needle cannula 20 is achieved by a non-conductive epoxy 34 or other such adhesive extending between distal end 32 of plastic tube 28 and the outer cylindrical surface of needle cannula 20. Epoxy 34 is chamfered to facilitate entry of needle assembly 12 into a patient. The chamfer preferably defines a length of about 1.0 mm.

Tube 28 includes a conductive layer 36 on its outer cylindrical surface which may be applied by plating or coating. Layer 36 preferably is gold and extends continuously from proximal end 30 to distal end 32 of tube 28 at a thickness of approximately 550 Angstroms. Needle assembly 12 effectively functions as a pair of coaxial conductors as explained further herein. In particular, stainless steel needle cannula 20 functions as an inner conductor, while gold layer 36 on tube 28 functions as an outer conductor. Tube 28 defines a non-conductive insulating material separating the inner and outer conductors defined respectively by stainless steel needle cannula 20 and gold layer 36.

As noted above, stainless steel needle cannula 12 extends continuously through stimulator 14, such that proximal end 22 of needle cannula 20 is disposed on one side of stimulator 14, while distal end 24 is disposed on the opposed side thereof. Proximal end 30 of plastic tube 28 is disposed within stimulator 14. As a result, both stainless steel needle cannula 12 and gold layer 36 are exposed for electrical contact within stimulator 14.

Stimulator 14 includes a generally rectangular housing 38 which can have length and width dimensions, for example, of approximately 0.781 inch and a thickness dimension, for example, of approximately 0.375 inch. Housing 38 can be formed from two molded thermoplastic housing halves 40 and 42 that are welded or adhered to one another. Top and bottom walls respectively may include concave regions to facilitate gripping by the digits of the hand.

Housing 38 performs multiple functions, including providing structural support for needle assembly 12, providing a convenient grip for manipulation of needle assembly 12 and safely enclosing the electronic components of the electrolocation apparatus 10.

The electronic circuitry of stimulator 14 includes an on/off switch 48 and a light emitting diode (LED) 50 both of which are accessible and/or visible from the exterior of housing 38. On/off switch 48 functions to complete circuitry between a battery and other portions of the circuitry as described further below, and optionally may permit switching between high and low charge levels. LED 50 is operative to generate a pulse of light with each pulse of electrical energy so that the technician or attending physician can compare energy pulses with muscle twitches in the patient.

Figure 3:
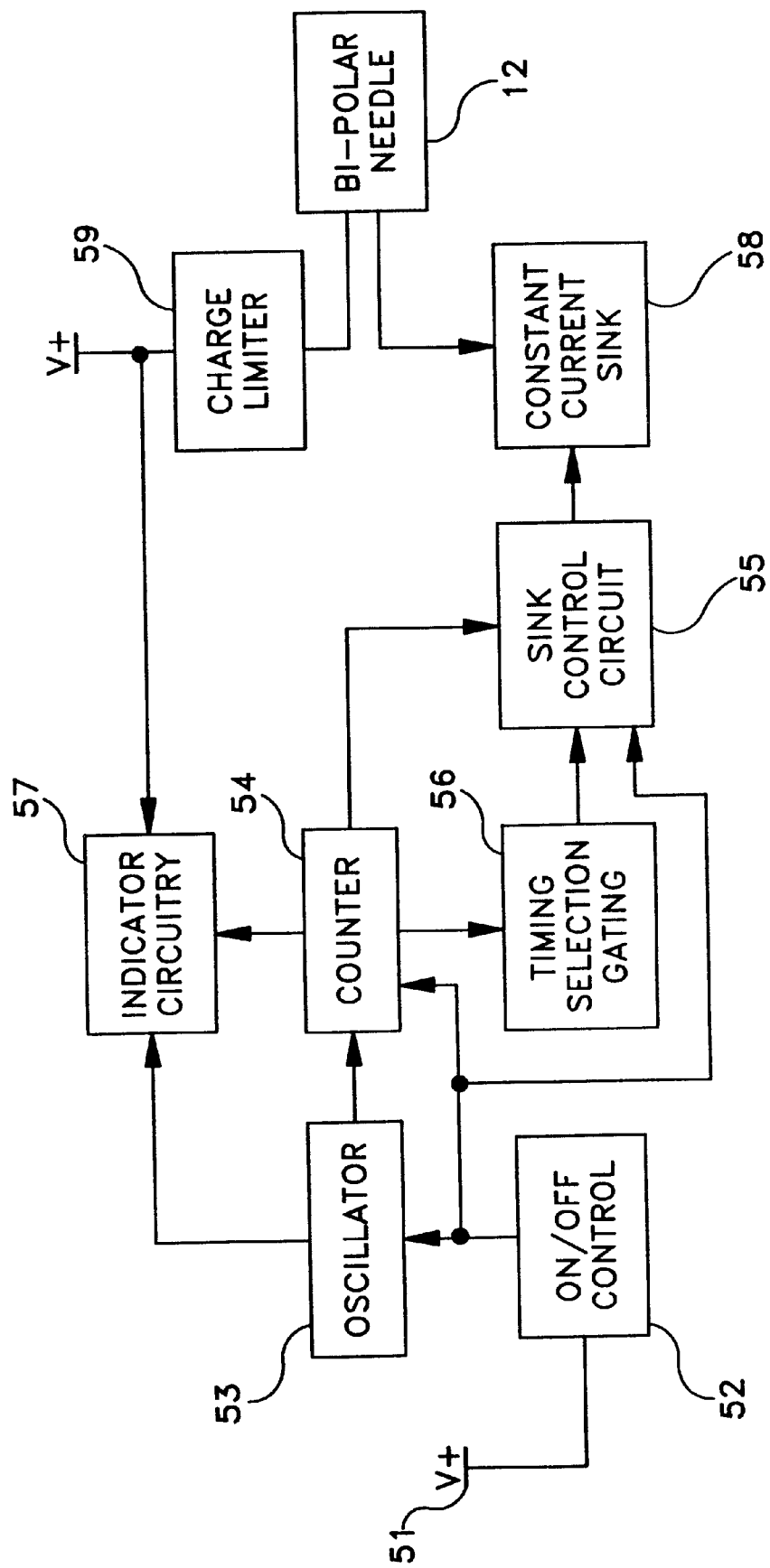
FIG. 3 is a block diagram of a set of circuit components which function to produce appropriate charge pulses across the needle of FIG. 2 in accordance with the subject invention.

FIG. 3 is representative of circuitry which can be used in stimulator 14. As the skilled artisan will appreciate, one way of implementing such circuitry is to digitize it, utilizing CMS technology as active elements. Other implementations, such as custom integrated circuits ("ICs") are also possible. Here, on/off switch 48 is connected to a three-volt lithium cell battery 52. In the off state, the quiescent current is under 1 microamps ("$\mu A$"), providing a battery life in excess of eight years, and thereby ensuring adequate shelf life for the electrolocation apparatus 10. In the on state, the oscillator and counter described below are enabled, and the battery will operate stimulator 14 for approximately 100 hours.

The time duration pulse modulation is achieved by a counter 54. Using the outputs of the counter 54, it is possible to generate a pulse as short as 122 $\mu S$. Since the outputs of the counter 54 are periodic signals, the Timing Selection Gating network 56 selects only one period of the output signal and applies it to the current source network 58. In the embodiment shown in FIG. 3, the gating network 56 may alternatively enable either one of a low charge pulse or one of a high charge pulse. As shown schematically in FIG. 5, stimulator 14 is operative to alternately generate short and long duration pulses. All of the pulses will be of a constant current, but will be of different durations. For example, stimulator 14 may be operative to generate a pulse at a current level of 0.2 mA for $\mu$S to produce a relatively low charge of 24.4 nanocoulombs ("nC"), followed by a current pulse of 0.2 mA for approximately 488 $\mu$S to produce a relatively high charge of 97 nC. It will be realized by the skilled artisan that depending on the components selected to generate the pulses, the duration of the pulses may vary within a range of time, for example, of about +/−20% of the durations stated herein. Other paired pulses of constant current for different durations may be used to produce alternating low and high charges.

The circuit of FIG. 3 also is designed to optionally provide constant duration pulses with current amplitude modulation. For example a low current pulse of 0.2 mA may be generated for 122 $\mu$S to produce a relatively low charge of 24.4nC and may be followed by a high current pulse of 0.8 mA for 122 $\mu$S to produce a relatively high charge of 97nC. It will be noted that the charges produced by the current level modulation option equal the charges produced by the time duration modulation option.

Figure 4:
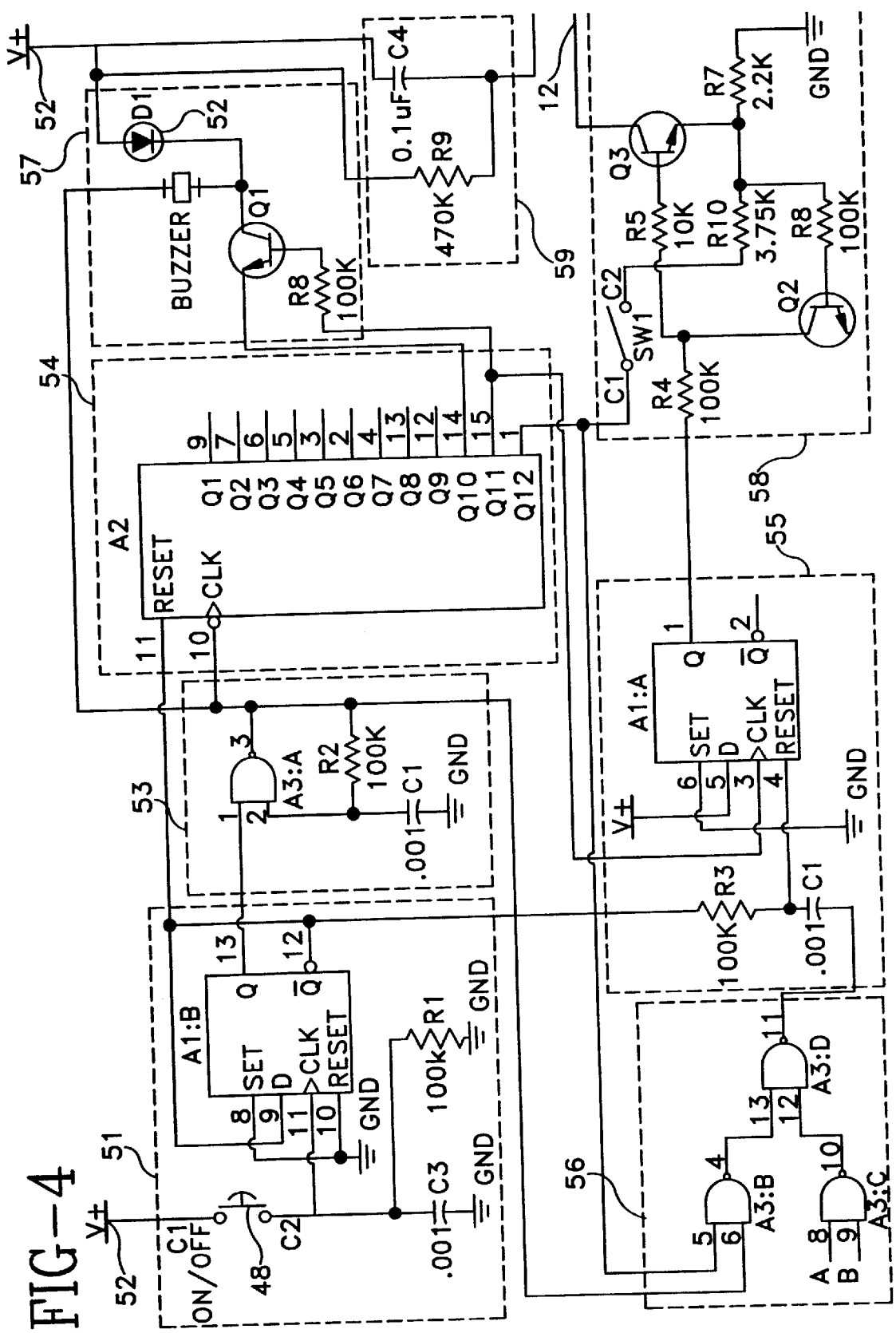
FIG. 4 illustrates an example of a combination of operative circuit components within the blocks of FIG. 3.

FIG. 3 is a block diagram of a set of circuit components, in stimulator 14, which function to produce appropriate charge pulses across bipolar needle 12, and FIG. 4 illustrates an example of a combination of operative circuit components within the blocks of FIG. 3. As seen in FIG. 3, an on/off control 51, actuated by switch 48, has an output that keys an oscillator 53 to activate a counter 54, and another output that enables and disables the counter 54. A third output is fed to a control circuit 55 which receives an output from the counter 54 and activates a constant current sink 58 coupled to one electrode (20 or 36) of the bipolar needle 12. Indicator circuitry 57, which drives LED 50, receives inputs from the oscillator 53, the counter 54, and the current source V+, which through a charge limiter 59 is coupled to the other electrode (36 or 20) of the bipolar needle 12. The timing and magnitude of the charge pulses are modulated by a Timing Selection Gating component 56 that is coupled to the control circuit 55.

Turning to the circuit details in FIG. 4, the on/off Control 51 may consist of the on/off switch 48 which couples the voltage V+ of battery 52 to circuitry including a flip-flop A1B and an RC (R1,C3) combination. When the apparatus 10 is to be used, the switch 48 is put in the on position and stays on to avoid any current surges at the needle. The flip-flop A1B controls the timing of the oscillator 53, which may comprise a Schmitt trigger A3A, and enables and disables the counter 54, which may be in the form of a 12-bit counter A2, and the sink control circuit 55, which may comprise a flip-flop A1A. When A1B is ON, output line 12 is low or 0, so the reset of counter A2 is off and thus it is free to count, and the reset of A1A is off so it is free to change state. Concomitantly, output line 13 of A1B is high or positive, so that the oscillator A3A operates, e.g., at 4.096 kilohertz ("kHz"), to cause counter A2 to count, whereupon pin 1 of A2 is caused to change state every ½ second and pin 15 goes positive every ½ second. Thus, pin 15 changes state at twice the rate of pin 1. When A1B is off, line 13 goes low, stopping the output of A3A, and line 12 goes high, resetting A2 and A1A.

When pin 15 of A2 goes positive, the clock signal to A1A causes output line 1 to go high, by voltage V+, supplying base current to transistor Q3, through resistors R4 and R5. Q3 is thereby caused to conduct closing a current path for current to flow through the needle 12 from the battery V+, across capacitor C4, and through resistor R7 to ground. If the voltage at R7 goes above 0.55 V, the base of transistor Q2 will be driven through resistor R6 to turn Q2 on, which in turn drops the base current to Q3, thus maintaining the voltage across R7 at 0.55 V. Accordingly, the current through the needle 12 is maintained substantially constant. In the event of a short or failure in the needle's current path, the capacitor C4 acts as a charge limiter by charging to a preselected maximum charge and limiting the current level.

The timing and form of the current pulses is determined through the use of the Timing Selection Gating component 56 which comprises three gates A3B, A3C, and A3D that receive inputs from the oscillator A3A and the counter A2 and provide an output to flip-flop A1A of the sink control circuit 55. Gate A3B controls the short pulses shown in the timing diagram of FIG. 5. It will be seen that input pin 10 to counter A2 works on negative pulses so that when the output of A3A, on pin 3, goes negative, output pin 15 of A2 goes positive driving A1A to turn on the current through the needle path as just explained above. The output on pin 3 of A3A is also supplied to input pin 6 of gate A3B, the other input pin 5 of which receives the output from pin 1 of A2. If the signal on pin 1 and in turn on pin 5 is high, A3B can function when pin 6 goes high. If pin 1 is low or at 0, then pin 5 is low and A3B cannot function. The operation of A3B can be used to control the alternating of the short and long charge pulses. When pin 1 is high, the short pulses will be produced.

More particularly, when pin 3 of A3A goes low, counter 54 will go to its next state. Pin 15 goes high so that current begins to flow through the needle and pin 1 is high so pin 5 of A3B is high, while pin 6 is low or 0 along with pin 3. The output of A3B on pin 4 will be 1, which is input on pin 13 to gate A3D. With a high input on pin 12, the output of gate A3D, on pin 11 will be 0. Now, when oscillator A3A outputs a high on pin 3, the counter A2 does not change its state, but pins 5 and 6 of A3B will both be high, so that the output on pin 4 will go to 0 causing the input to pin 13 to be 0. If the input on pin 12 is still high, the output of A3D on pin 11 goes high. The high signal on pin 11 is coupled through capacitor C2 to the reset of flip-flop A1A causing its output on pin 1 to got to 0, turning off the constant current sink 58 and the current through the needle 12. A short current pulse will then have been produced of 122 $\mu$S duration.

To produce the longer pulses, gate A3C is used and gate A3B is disabled. Since A3B can only function when pin 1 of A2 is high, the signal on pin 1 is caused to go low turning A3B off. In this condition the reset function of A1A is controlled only by A3C. The output of A3C may be controlled according to the pulse ratio table shown adjacent to A3C in FIG. 4. By appropriately connecting the A (8) and B (9) inputs of A3C to the listed combination of pins of counter A2, the time ratios between the short and long pulses shown in the left hand column of the table can be achieved, thus accomplishing pulse width modulation of the charge pulses.

For accomplishing pulse amplitude modulation, the A and B inputs to A3C can both be connected to pin 10 of A2 to produce a pulse time ratio of 1 to 1, the pulses being of 122$\mu$S. A resistor R10 in the constant current sink 58 is connected into the circuit between pin 1 of A2 and the emitter of transistor Q3 by closing a switch SW1. When pin 1 is high, current flows through R10 and resistor R7 to ground. The current in the current path through the needle 12 is thus decreased since the voltage across R7 remains constant and the current through R7 is made up of two sources. Consequently, the magnitude of the current pulse across needle 12 becomes a comparatively low current pulse. When pin 1 of A2 is low, i.e., goes to ground, R10 is configured in parallel with R7 with respect to ground, so that the resistance across R7 and R10 drops with respect to the current path. Since the voltage of 0.55 V is maintained at their junction point, as explained above, more current is needed across both resistors. Thus, the magnitude of the current pulse across the needle 12 is increased resulting in a comparatively high current pulse. Accordingly, pulse amplitude modulation can be accomplished with this circuitry.

If desired, both pulse width and pulse amplitude modulation can be produced by selection of the pulse ratios in the pulse ratio table and the switching of resistor R10 into the circuit.

Lastly, the indicator circuitry 57 is configured to activate whenever a pulse has been produced, irrespective of the modulation, and to produce a simple on or off indication. Thus, the LED 50 will flash ON upon the occurrence of a charge pulse or the buzzer 60 will produce a sound in accordance with the timing and state change of the outputs on pin 3 of A3A and pin 15 of A2.

As noted above, proximal end 22 of stainless steel needle cannula 20 projects entirely through housing 38 of stimulator 14. As shown in FIG. 1, proximal end 22 of stainless steel needle cannula 20 is connected to flexible tubing 16 which extends to a hub that is connectable to a syringe for delivering a selected dose of anesthetic. In an alternate embodiment, proximal end 22 of stainless steel needle cannula 20 may be mounted directly to a needle hub that is connectable to a syringe for administering a selected dose of anesthetic.

In use, an anesthesiologist or nurse anesthetist inserts the beveled distal tip 24 of stainless steel needle cannula 20 into a patient and toward the targeted nerve. No conductive pad and no wires are used. In the constant current embodiment described herein, the switch 48 on the stimulator 14 is then actuated to generate the low constant current pulses of electrical energy. Proper functioning of the electrolocation apparatus 10 is confirmed by the flashing LED 50 generating a pulse of light concurrent with each respective pulse of energy. The respective pulses of energy are generated at ½ second intervals. The high charge pulses of 0.2 mA for 488 $\mu$S will generate a charge of 97 nC. The low charge pulses are of the same 0.2 mA current, but last for only 122 $\mu$S and will generate a charge of only 24.4 nC. The higher charge pulses of 97 nC will be sufficient to generate observable muscle twitches at a substantially superficial location after the skin has been penetrated by the gold layer 34, while the lower charges, pulses of 24.4 nC will not be sufficient to initially generate any observable muscle twitches at this distance from the nerve. Thus, the anesthesiologist or nurse anesthetist will observe muscle twitches at approximately one second intervals coinciding with the high charge pulses.

The needle assembly 12 is urged further toward the targeted nerve. This advancement of the needle assembly 12 will show a gradual increase in the magnitude of the twitches occurring at one second intervals. However, these twitches in response to the high charge will soon peak. The anesthesiologist or nurse anesthetist then will observe small magnitude muscle twitches between the larger magnitude twitches. Thus, alternating small and large magnitude twitches will be readily observable.

As the needle assembly 12 is further advanced into the patient, the small magnitude muscle twitches will increase in magnitude to approach the magnitude of the peaked large magnitude muscle twitches generated by the high charge pulses. As the distal tip 24 of the stainless steel needle cannula 20 nears the targeted nerve, the muscle twitches generated in response to the low charge pulses will be substantially indistinguishable from the muscle twitches generated in response to the high charge energy pulses.

Thus, the anesthesiologist or nurse anesthetist will observe substantially identical muscle twitches at 0.5 second intervals. This readily observable response will indicate to the anesthesiologist or nurse anesthetist that the beveled distal tip of needle cannula 20 is sufficiently close to the targeted nerve for administration of the anesthetic. The anesthetic is delivered in the conventional manner by actuation of the hypodermic syringe communicating with the proximal end 22 of stainless steel needle cannula 20.

The exact procedure can be carried out by the alternate embodiment which modulates current level.

While the invention has been described with respect to a preferred embodiment, it is apparent that various changes can be made without departing from the scope of the invention as defined by the appended claims. For example, the stimulator may have switch mechanisms for changing the current level or the pulse width to vary the respective levels of the charges delivered to the patient. Additionally, other indications of pulse generation may be provided, including an audible buzzer in place of or in addition to the LED described above.

Figure 5:
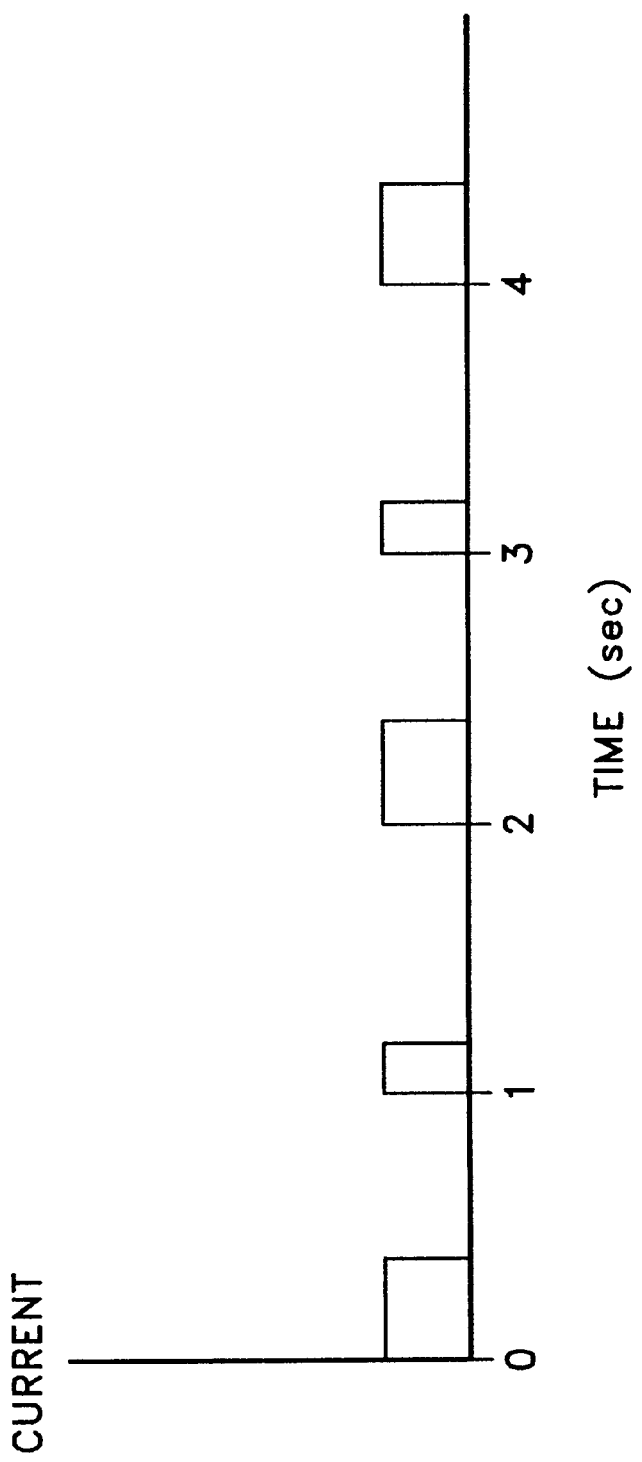
FIG. 5 is a graph showing a pulse generation pattern in accordance with the subject invention.

Referring to FIGS. 6–11c, another preferred embodiment of the self contained electrolocation apparatus is illustrated. In this embodiment several of the components of the circuit disclosed in FIGS. 3–5 are replaced by a microprocessor, however, many components of the self-contained electrolocation apparatus are similar and perform similar functions. The replacement of several of the discrete components by a microprocessor provides the capabilities for the electrolocation apparatus of the invention as described below. In the description of this embodiment, the term "proximal" is used to describe those parts of the device closest to the practitioner and the term "distal" is used to describe those parts of the device furthest from the practitioner. Additionally, a series of reference characters beginning with 100 are used to identify components in FIGS. 6–11c.

Figure 6:
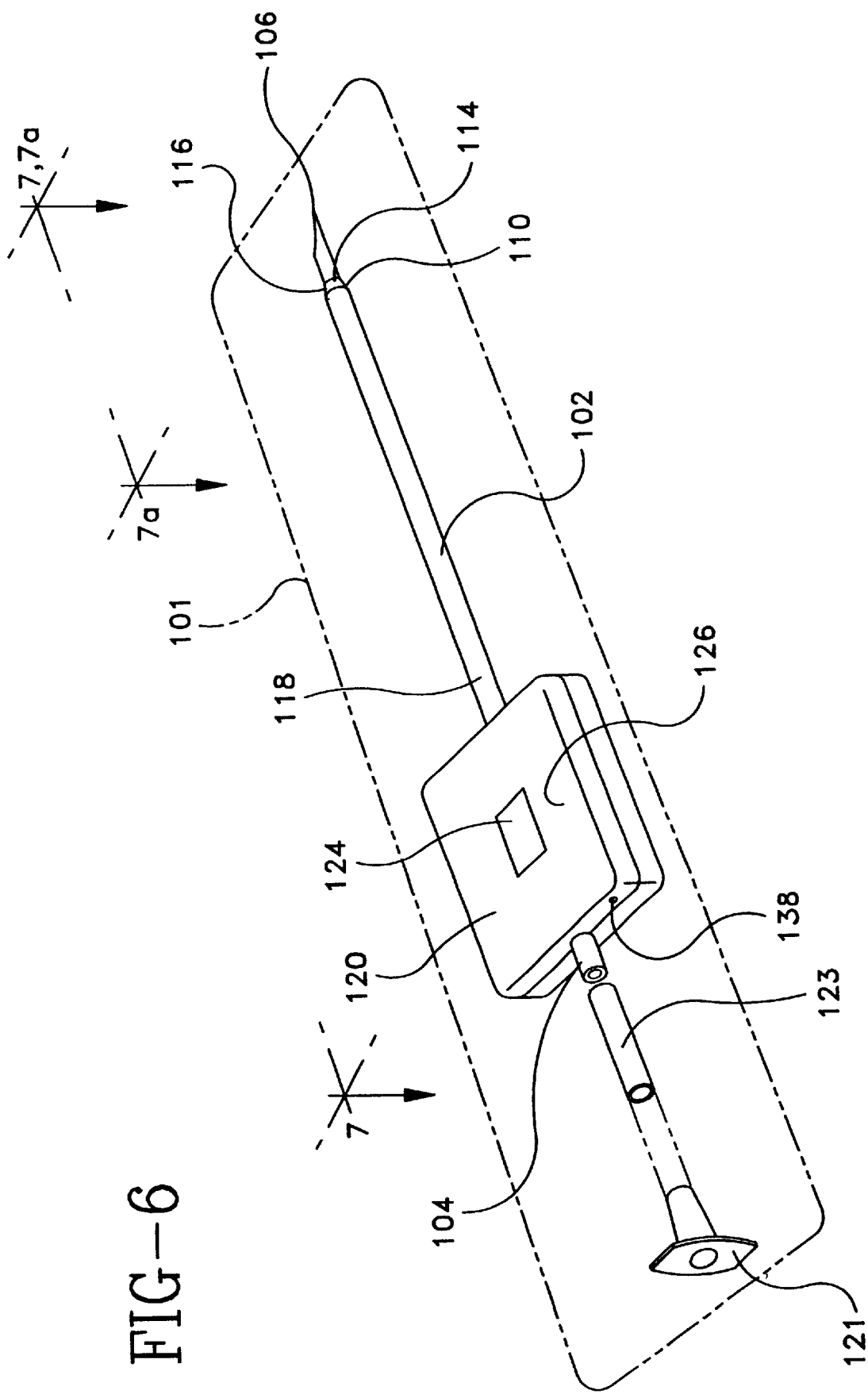
FIG. 6 is a perspective view of an alternate preferred embodiment of the electrolocation apparatus of the invention.

As shown in FIGS. 6, 7 and 7a, a self-contained electrolocation apparatus 100 of the present invention includes an electrically conducting needle cannula 102 having a proximal end 104, a distal end 106 and a hollow bore 108 therethrough. Preferably, distal end 106 of the needle cannula is formed into a sharpened point to facilitate penetration of the patient's tissue by the needle cannula. Apparatus 100 includes a non-conductive tube 110 having a proximal end 112 and a distal end 114. Tube 110 is mounted over needle cannula 102 so that distal end 114 of non-conductive tube 110 is proximal to distal end 106 of the needle cannula. Preferably, tube 110 is fixedly attached to needle cannula 102 by an adhesive 116 that forms a chamfer 117 at distal end 114 of the tube 110 to facilitate introduction of the needle cannula into a patient's tissue. Non-conductive tube 110 has a conductive layer 118, thereon having a distal end 119, whereby needle cannula 102 and conductive layer 118 respectively define first and second conductors coaxially spaced from one another by non-conductive tube 110. Preferably, conductive layer 118 is formed by applying a conductive material such as a layer of gold, and the like, or other highly conductive and inert material. Preferably, conductive layer 118 is applied by vacuum deposition, electroplating and the like.

There is a grip 120 fixedly attached to needle cannula 102 for manipulating the apparatus. Grip 120 has an electrical stimulus generator circuit 122 within it that is electrically connected to first conductor 102 and second conductor 118. Stimulus generator circuit 122 is capable of applying a potential across the conductors so that when needle 102 is positioned in the patient's tissue and electrical stimulus generator circuit 122 is activated, the potential is sufficient to induce a preselected current thereby providing a charge pulse between distal end 119 of conductive layer 118 and the distal end 106 of needle cannula 102 through the patient's tissue. The charge pulse is sufficient to induce a twitch response in the patient.

Preferably, apparatus 100 is placed in a package 101, indicated in phantom in FIG. 6, formed from materials substantially resistant to microorganisms and exposed to conditions that render any microorganisms inside the package substantially non-viable. Suitable materials for forming package 101 include, but are not limited to paper, non-woven composite materials, polymeric films, metallic foils and composites thereof. Suitable conditions for rendering microorganisms non-viable include exposure to heat, ionizing radiation and chemical agents such as ethylene oxide and gaseous hydrogen peroxide. Preferably, ethylene oxide exposure is used. For particular applications, other sterilization techniques may be preferred.

Apparatus 100 includes an attachment 121 for attaching a fluid handling device such as a syringe. Preferably, attachment 121 includes a female luer fitting. Generally, it is preferred that attachment 121 be isolated from grip 120 by a length of flexible tubing 123 as shown in FIG. 6. The reason for isolating the fluid handling device from grip 120 is to substantially reduce any movement of the position of distal end 106 of the needle in relation to a target nerve during administration of a medicament once the nerve has been located.

Figure 8:
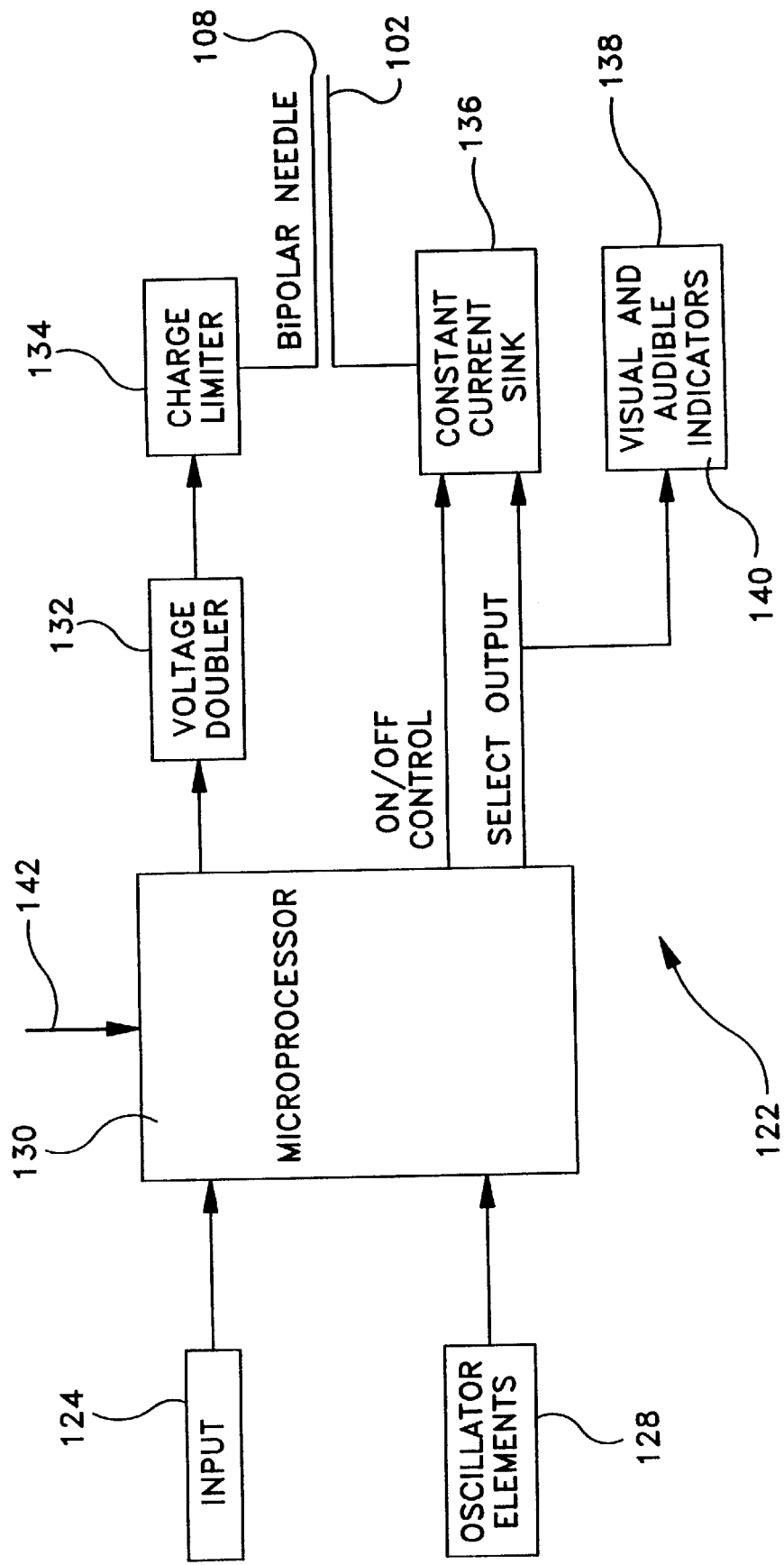
FIG. 8 is a block diagram of an alternative embodiment of the electrical stimulus generator circuit self-contained electrolocation apparatus of the invention.

Referring to FIGS. 6–9, stimulus generator circuit 122 as described in a functional block diagram in FIG. 8, includes an input device 124, that is preferably a momentary contact switch accessible to a practitioner's finger pressure by squeezing an outside surface 126 of grip 120. Circuit 122 further includes oscillator elements 128. Both input device 124 and oscillator elements 128 are electrically connected to a microprocessor 130 that is programmed to control the potential applied across the conductors, the current delivered and the duration of the current to preselected values. Circuit 122 further includes a voltage doubler 132, a charge limiter 134, a constant current sink 136 and, preferably, a visible indicator 138 and an audible indicator 140 of the function of the circuit. A more detailed schematic drawing of circuit 122 is provided in FIG. 9. Preferably, some or all of the elements including, but not limited to, oscillator elements 128, charge limiter 134 and constant current sink 136 indicated in the functional block diagram, may be integrated into microprocessor 130 if the microprocessor is a custom fabrication.

Figure 9:
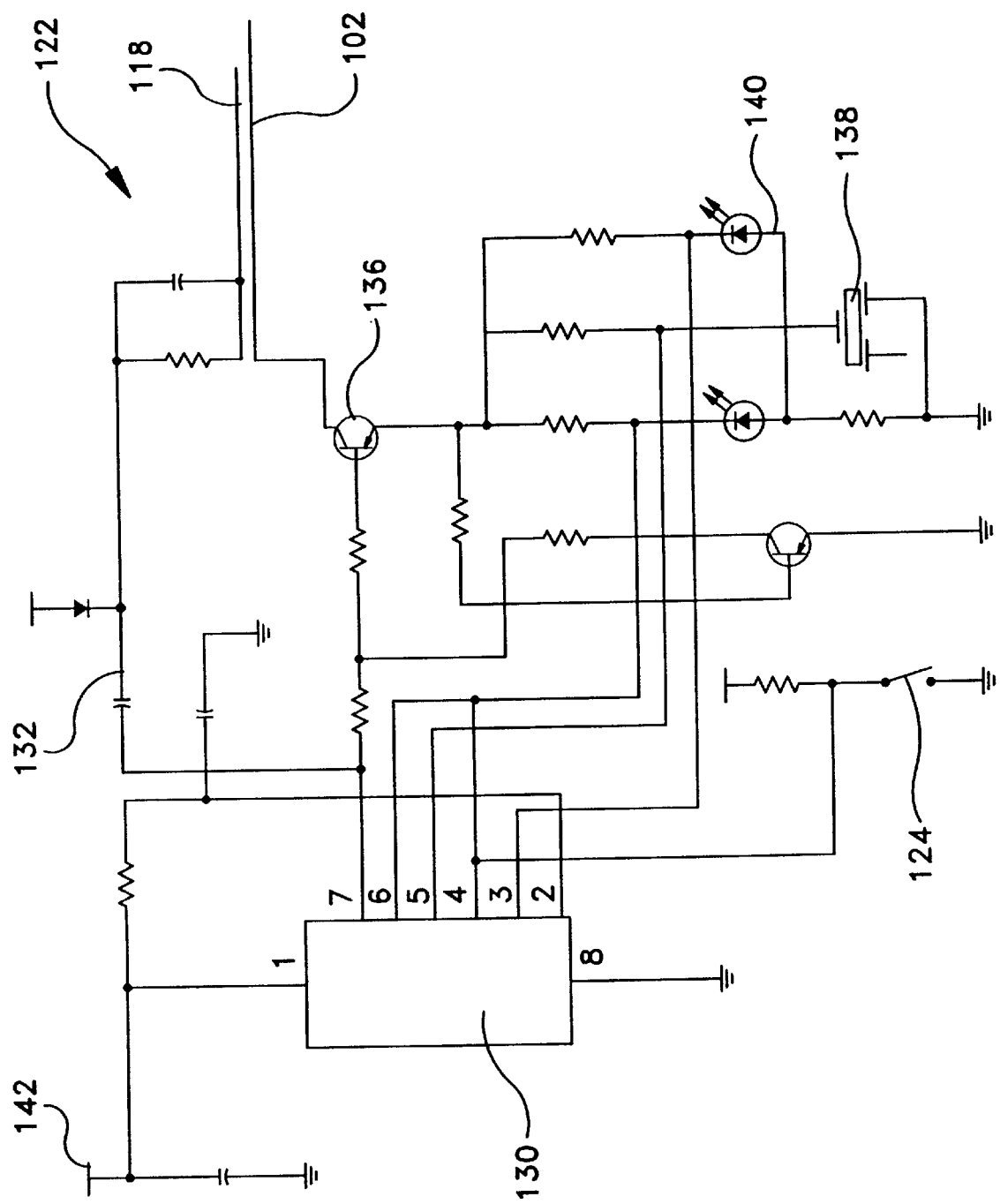
FIG. 9 is a circuit diagram of the electrical stimulus generator circuit of the self-contained electrolocation apparatus of FIG. 6.
Figure 10B:
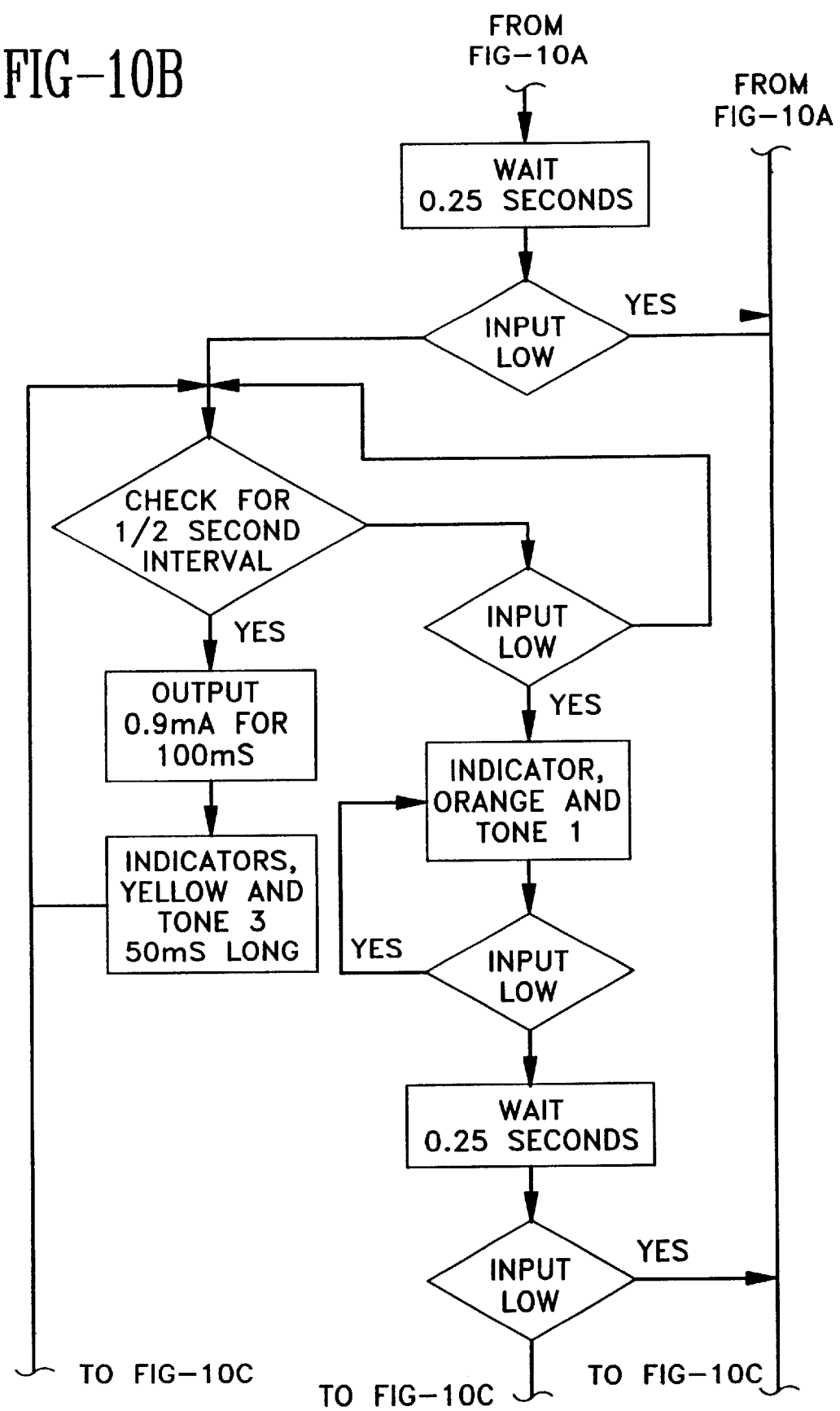

Circuit 122 as disclosed in FIG. 9 is capable of providing a plurality of functions as illustrated schematically in FIGS. 10a–c. Circuit 122 as disclosed in FIGS. 8 and 9 is not to be considered as limitative of the invention, rather, circuit 122 is exemplary of the function of self-contained locator assembly 100. Other circuits with other components may be envisioned to perform similar functions and are considered to be within the scope of the invention. Suitable one time programmable micro-controllers useful as microprocessor 130 for circuit 122 include, but are not limited to, PIC 12C508 available from Microchip Technologies, Chandler, AZ and COPS 8-pin connection micro-controllers available from National Semiconductor in California. Preferably, microprocessor 130 is a PIC 12C508 from Microchip Technologies. Circuit 122 includes a power source such as a battery 142 with a long shelf life. Suitable batteries include lithium cells, silver oxide cells and the like. Preferably, battery 142 is a three volt CR1620 lithium cell.

Circuit 122 applies voltage potentials between conductive layer 118 and conductive needle 102 so that when apparatus 100 is in use with distal ends 106 and 119 positioned in a patient's tissue, an electrical current forming a charge pulse is generated through the patient's tissue between distal end 106 of the conductive needle and distal end 119 of the conductive layer. Preferably, electrical stimulus generator circuit 122 provides a plurality of repeatable patterns in a plurality of operating modes. A practitioner activates electrical stimulus generator circuit 122 by sequentially squeezing momentary contact switch 124 to provide input to microprocessor 130. Circuit 122 also preferably includes an indication of the operating mode of the circuit such as transducer 138 to provide an audible sound and visible radiative element 140 that emits visible light. Preferably, visible radiative element 140 is a multi-color light emitting diode (LED) that provides the practitioner with positive identification that device 100 is, functioning and identifies the operating mode.

Referring to FIGS. 10a–c and 11a–11c, preferably, circuit 122 continuously operates once battery 142 is installed and power is applied to the circuit. The continuous power-on state substantially avoids the possibility of the circuit producing a spark when the circuit goes from an unpowered state to a powered state as would be the case if an on/off switch were used. Circuit 122 preferably, once powered, goes into a "sleep" mode with a current draw of less than about 1 microamp. In this sleep mode, the life of battery 142 is substantially equal to the battery's normal shelf life, which for the preferred lithium battery is nearly eight years, thus providing an apparatus 100 with a predicted fully functional shelf life of at least 5 years. Preferably, apparatus 100 additionally has three operating modes wherein circuit 122 applies potentials to conductive needle 102 and conductive layer 118 and a quiescent mode, wherein no potential is applied to needle 102 and conductive layer 118. Further, microprocessor 130 preferably is programmed so that circuit 122 delivers a preselected total operating time directable to conductive needle 102 and conductive layer 118, after which the circuit directs the output only to radiative element 140 until the battery potential is substantially dissipated. Preferably, the preselected total operating time is sufficient to allow a practitioner sufficient time to complete a procedure, after which apparatus 100 is no longer functional. Once the processor shifts the output to the radiative element, apparatus 100 is actively rendered of no further use, thereby precluding any issues of reuse contamination or questions of disposal of active batteries. Preferably, the preselected total operating time is about two hours.

The practitioner uses momentary contact switch 124, to provide input to microprocessor 130 to sequentially select between the operating modes and the quiescent mode. Referring to the program flow diagram illustrated in FIG. 10, the several modes of circuit 122 are schematically displayed. FIGS. 11a–c schematically illustrate the charge pulsed output of circuit in the several operating modes. In FIGS. 11a–c, the X-axis indicates time and the Y-axis indicates current in milliamps (mA). Preferably, with every input, i.e., squeeze of momentary contact switch 124, the multicolor LED radiative element 140 provides an orange color and transducer 138 provides an audible tone. As shown in FIG. 10, the first momentary contact initiates the total operating time sequence and shifts processor 130 to a first operating mode wherein a series of charge pulses (as illustrated in FIG. 11a) are provided. Preferably, the charge pulses in operating mode one are constant current, of uniform duration and are uniformly spaced. The first operating mode charge pulses are preferably about 1.8 mA current for about 100 microsecond duration at a rate of about two pulses per second. The charge pulses in the first operating mode provide about 180 nanocoulombs. During operation in the first operating mode, radiative element LED 140 preferably indicates red 50 millisecond flashes and transducer 138 produces about 50 millisecond duration audible tones at a rate substantially similar to the charge pulses.

When the practitioner provides a second momentary contact of input device 124, radiative element 140 indicates orange, transducer 138 provides the audible tone, and circuit 122 shifts to a second operating mode (illustrated in FIG. 11b) with charge pulses of about 0.9 mA current with about 100 microsecond duration at a rate of about two pulses per second. The charge pulses in the second operating mode provide about 90 nanocoulombs. In the second operating mode, radiative element LED 140 preferable indicates yellow 50 millisecond flashes and transducer 138 produces about 50 millisecond duration audible tones at a rate substantially similar to the charge pulses.

When the practitioner desires to shift to a third operating mode, a third activation of momentary contact input device 124 again causes radiative element LED 140 to indicate orange, transducer 138 produces the audible tone, and circuit 122 shifts to the third operating mode. In the third operating mode (illustrated in FIG. 11c) with charge pulses of about 0.3 mA current alternating durations between about 100 microseconds and 130 microsecond duration at a rate of about two pulses per second. In the third operating mode, circuit 122 provides between about 30 and 39 nanocoulombs. In the third operating mode, radiative element LED 140 preferably indicates green 50 millisecond flashes and transducer 138 produces about 50 millisecond duration audible tones. The purpose of the alternating duration pulses is to provide alternating intensity charge pulses. If the needle is positioned in close proximity to the target nerve, the twitch response seen in the patient continues at a rate of two twitches per second. If the needle is not positioned in close proximity to the target nerve, the twitch response may change to one twitch per second in the third mode, as only the higher intensity pulse is sufficient to induce the twitch response if the needle is not in close proximity to the target nerve. In the third mode, the practitioner may also observe twitch pulses of alternating higher and lower intensity.

A subsequent operation of momentary contact input device 124 causes radiative element 140 to indicate orange, transducer 138 to provide an audible tone and returns circuit 122 to the second operating mode. Further single activations of momentary contact input device 124 allow the practitioner to cause circuit 122 to alternate between the second and the third modes. If the practitioner desires the output charge pulses to cease, at any point during the sequences, the practitioner may apply a rapid double activation (i. e., a "double-click") of input device 124, accompanied by radiative element 140 indicating orange flashes and transducer 138 producing tones, to cause circuit 122 to shift to the quiescent state. Following this shift to the quiescent state, circuit 122 may be sequentially returned to each of the operating modes starting with the first operating mode following the same procedure described above. Preferably, no matter which one of the operating modes or the quiescent mode is selected by the practitioner, circuit 122 does not operate longer than the preselected total operating time, substantially rendering the device capable only of a single-use.

The operating modes and the quiescent mode described above are intended to be representative and illustrative, not limitative, of the capabilities of apparatus. For particular applications, other preselected current values, pulse durations, pulse rates, indicator colors and audible tones may be selected and are considered to be within the scope of the invention. Generally, effective preselected constant currents are between about 0.1 milliamps to about 2 milliamps. Pulse durations between about 50 microseconds and 1,000 microseconds have been shown to be effective for electrolocation of nerves and the time intervals between the pulses are generally effective between about 0.25 seconds to about 2.0 seconds.

A method for using apparatus 100 includes the practitioner removing apparatus 100 from package 101 and activating input device 124 by squeezing grip 120, observing the orange flash from radiative device 140 and the audible tone from transducer 138. Circuit 122 is now in the first operating mode and applying a potential between cannula 102 and conductive layer 118 and providing a flashing red indication and audible tone to the practitioner. The practitioner positions apparatus 100 in the patient's axillary area and advances the distal point of needle 102 into the patient's tissue. As distal end 106 of the cannula approaches the target nerve in the patient, the charge pulses result in a sympathetic twitch reflexive movement in the patient's arm. The practitioner then may select a lower intensity pulse by squeezing grip 120 observing the orange flash and the audible tone as circuit 122 changes to the second operating mode with yellow flashes and audible tones. The practitioner further advances the needle to close proximity to the target nerve and again squeezes grip 120 to activate input device 124 and shift circuit to the third operating mode. The practitioner is able to observe the green flash and tone corresponding to the pulses of the third operating mode. Since the third operating mode preferably has alternating charge pulses, the practitioner can determine the proximity to the target nerve by observing the sympathetic reflexive twitches in the patient's arm. If the twitches continue at about 2 twitches per second, the distal tip is close to the target nerve, if the practitioner observes the twitches at only one twitch per second, the distal tip of the cannula is probably not in close proximity to the target nerve, since only the alternate higher intensity pulses are sufficient to induce the sympathetic twitch response in the patient. When the practitioner is satisfied that the needle is properly positioned, an anesthetic agent may be administered and, if the positioning is proper, the twitch response ceases as the anesthetic agent takes effect.

As described above, preferably battery 142 is about three volts. Use of a three volt battery enables the device to be physically small and contributes to the substantially inherent safety of apparatus 100 in combustible atmospheres such as may be found in the presence of some gaseous anesthetic agents. However, in order to obtain currents of about 1.8 mA as used in the first operating mode, circuit 122 includes voltage doubler 132 to provide sufficient potential for the higher current pulses. Use of voltage doubler 132 to provide the higher potential necessary for the higher current pulses coupled with the close proximity of distal end 106 of cannula 102 to the distal end 119 of conductive layer 118 provides sufficient potential to provide the desired currents. Other currently available electro stimulation nerve locator devices employ a single electrode needle with a secondary patch type electrode remotely located on the patient's body to complete the circuit. Since the current pathway is necessarily much longer and less focused in the area of the target nerve in these devices than with the present invention and the secondary patch type electrode is located on the outside surface on the skin of the patient's body, the electrical resistance encountered in completing the circuit for the currently available devices is significantly higher than with the present invention. Thus, these currently available devices require a significantly higher potential voltage source than the preferred apparatus 100 three volt battery to generate the required currents. Many of these currently available devices utilize potentials of up to about 30 volts. Because of the higher power requirements and the reusability, the currently available devices are physically at least as large as a pack of cigarettes and often have multiple batteries. Currently available devices generally use sterile disposable needles and disposable patch electrodes, but because of the power requirements, the electro stimulus circuit component is reusable, has an on/off switch that turns off the power to the circuit and requires connecting wires and plug connectors of some type.

In actual use of the currently available devices, one recurring problem is that, when the practitioner attempts to perform a procedure with the reusable device, the battery is found to be discharged to the point where it is incapable of delivering sufficient power for the procedure. Other problems with the current reusable devices are that the devices are subject to damage by dropping as well as requiring cleaning and sanitation between being used. Additionally, currently available reusable devices require the institution to maintain the device under some type of maintenance, regular testing and calibration protocol. During use in a procedure, the currently available reusable devices generally require the presence of a technician or other assistant to the practitioner for their use because the practitioner cannot manipulate the needle and adjust the remote stimulator device at the same time. Currently available high power nerve locator devices with remote electrode patches are contraindicated in patients with cardiac pacemakers because the current pathway between the needle tip and the remote patch electrode may interfere with the stimulus provided to the patient's heart by the cardiac pacemaker.

Apparatus 100 of the invention provides solutions to many of the problems found with the currently available devices. Apparatus 100 is readily used by only one practitioner because the stimulus generator circuit has its controls, as well as visible and audible indications of its function contained within the grip used to manipulate the device. As long as apparatus 100 is used within its recommended shelf life, it substantially always has a fully charged battery. When using apparatus 100 of the invention, the practitioner does not need to concern himself about whether or not the device has been properly cleaned and tested. Apparatus 100 is supplies sterile and is capable only of a single-use. Additionally, since both electrodes of apparatus 100 are in close proximity to one another, the current pathway flow is substantially only between the distal tip of the first conductor and distal tip of the second conductor. Accordingly, it is believed, but not yet proven, because of the short current flow pathway, the apparatus of the invention is substantially unlikely to cause interference with cardiac pacemakers or other implanted devices with electronic components.

What is claimed is:

1. A self-contained electrolocation apparatus comprising:
   an electrically conducting needle cannula having a proximal end, a distal end and a hollow bore therethrough;
   a non-conductive tube having a proximal end and a distal end, said tube mounted over said needle cannula so that said distal end of said non-conductive tube is proximal to said distal end of said needle cannula;
   a conductive layer having a distal end on said non-conductive tube, whereby said needle cannula and said conductive layer respectively define first and second conductors coaxially spaced from one another by said non-conductive tube;
   a grip fixedly attached to said needle cannula for manipulating said apparatus; and
   an electrical stimulus generator circuit within said grip and electrically connected to said first conductor and said second conductor, said stimulus generator being capable of applying a potential across said conductors so that when said needle is positioned in a patient's tissue and said electrical stimulus generator circuit is activated, said potential is sufficient to induce a preselected current thereby providing a charge pulse between said distal end of said conductive layer and said distal end of said needle cannula through the patient's tissue, said charge pulse being sufficient to induce a twitch response in the patient.

2. The electrolocation apparatus of claim 1 wherein said electrical stimulus generator circuit comprises a microprocessor.

3. The electrolocation apparatus of claim 2 wherein said electrical stimulus generator circuit provides said preselected charge pulses in at least one preselected repeatable pattern in at least one operating mode.

4. The electrolocation apparatus of claim 3 wherein said electrical stimulus generator circuit provides a plurality of repeatable patterns in a plurality of operating modes.

5. The electrolocation apparatus of claim 4 wherein said stimulus generator circuit further comprises an input device accessible by a practitioner's finger pressure thereby allowing the practitioner to select one of said operating modes.

6. The electrolocation apparatus of claim 5 wherein said input device is a momentary contact switch.

7. The electrolocation apparatus of claim 6 wherein said momentary contact switch allows the practitioner to select sequentially from three preselected patterns of charge pulses and one quiescent mode.

8. The electrolocation apparatus of claim 7 wherein said preselected patterns include charge pulses of different currents.

9. The electrolocation apparatus of claim 8 wherein said currents associated with said charge pulses within one preselected pattern are constant.

10. The electrolocation apparatus of claim 9 wherein said preselected constant currents are between about 0.1 milliamps to about 2 milliamps.

11. The electrolocation apparatus of claim 10 wherein said preselected patterns include pulses of different durations.

12. The electrolocation apparatus of claim 11 wherein said durations of said pulses are between about 50 microseconds and 1,000 microseconds.

13. The electrolocation apparatus of claim 12 wherein said preselected pattern of charge pulses includes preselected time intervals between said pulses.

14. The electrolocation apparatus of claim 13 wherein said preselected time intervals are between about 0.25 seconds to about 2.0 seconds.

15. The electrolocation apparatus of claim 2 wherein said stimulus generator circuit includes means for ensuring that said electrolocation apparatus, once used for a procedure, is substantially prevented from being used for more than a preselected time period; and said time period being sufficient for a practitioner to complete one procedure, thereby rendering said electrolocation apparatus substantially single-use.

16. The electrolocation apparatus of claim 15 wherein said means for ensuring that said electrolocation apparatus once used for a procedure is substantially prevented from being used for more than a preselected total operating time period comprises prograrnning said microprocessor to direct said potential to a radiative element after said preselected total operating time has elapsed until said potential is substantially depleted.

17. The electrolocation apparatus of claim 1 wherein said electroconductive cannula projects proximally beyond said grip and includes a connector for connecting a medication delivery device to said bore of said electroconductive needle.

18. The electrolocation apparatus of claim 17 wherein said connector further includes a flexible tube.

19. The electrolocation apparatus of claim 1 wherein said stimulus generator circuit further comprises an indicator of said charge pulse.

20. The electrolocation apparatus of claim 19 wherein said indicator fiurther comprises a transducer to produce a sound audible to the practitioner using said apparatus.

21. The electrolocation apparatus of claim 19 wherein said indicator further comprises a radiative element to produce a light emission visible to a practitioner using said apparatus.

22. The electrolocation apparatus of claim 1 wherein said stimulus generator circuit further comprises a battery.

23. The electrolocation apparatus of claim 22 wherein said battery has a maximum potential of about three volts.

24. The electrolocation apparatus of claim 23 wherein said stimulus generator circuit further comprises a voltage doubler circuit to provide about six volts maximum potential between said first conductor and said second conductor.

25. The electrolocation apparatus of claim 1 wherein said stimulus generator circuit is always operating once powered thereby providing a substantially inherently safe circuit, and further comprises a sleep mode having a minimum power draw so that said apparatus has a shelf life substantially limited by a shelf life of the battery.

26. The electrolocation apparatus of claim 1 being sealed in a package formed from a material substantially resistant to the passage of microorganisms and exposed to conditions rendering any microorganisms therein substantially non-viable, thereby providing said apparatus in a substantially sterile state until said package is opened.

27. A self-contained electrolocation apparatus comprising:
an electrically conducting needle cannula having a proximal end, a distal end and a hollow bore therethrough;
a non-conductive tube having a proximal end and a distal end, said tube mounted over said electroconductive needle so that said distal end of said non-conductive tube is proximal to said distal end of said needle cannula;
a conductive layer on said non-conductive tube whereby said needle cannula and said conductive layer respectively define first and second conductors coaxially spaced from one another by said non-conductive tube;
a grip fixedly attached to said needle cannula for manipulating said apparatus; and
an electrical stimulus generator circuit including a battery within said grip and electrically connected to said first conductor and said second conductor, said stimulus generator circuit including an input device accessible by a practitioner's finger pressure to select an operating mode from a plurality of operating modes of said stimulus generator circuit, said stimulus generator being capable of applying a potential across said conductors sufficient to generate charge pulses, said circuit further including indications visible and audible to a practitioner of said preselected charge pulses, so that when said needle is positioned in a patient's tissue the practitioner can initiate and terminate one of said patterns of charge pulses and is informed of the status of said generator circuit, and wherein said charge pulses are sufficient to induce preselected constant currents between said distal end of said conductive layer and said distal end of said conductive needle through the patient's tissue, said currents being sufficient to induce a twitch response in the patient.

28. An electrolocation apparatus comprising:
an electrically conducting needle cannula having a proximal end, a distal end and a hollow bore therethrough; and
an electrical stimulus generator circuit electrically connected to the needle for generating charge pulses of electrical energy alternating between high and low charge pulses, wherein the alternating charge pulses are generated by varying the time duration of the pulses.

29. The electrolocation apparatus of claim 28, wherein the charge pulses are approximately constant.

30. The electrolocation apparatus of claim 29, wherein the time duration of the low charge pulse is between about 95 to 150 microseconds.

31. The electrolocation apparatus of claim 30, wherein the time duration of the high charge pulse is between about 375 to 600 microseconds.

32. An electrolocation apparatus comprising:
an electrically conducting needle cannula having a proximal end, a distal end and a hollow bore therethrough; and
an electrical stimulus generator circuit electrically connected to the needle for generating charge pulses of electrical energy alternating between high and low charge pulses, wherein the alternating change pulses are generated by varying the current level of the charge pulses.

33. The electrolocation apparatus of claim 32, wherein the time duration of the charge pulses are approximately the same duration.

34. The electrolocation apparatus of claim 33, wherein the low current pulses are less than or equal to about 0.2 mA.

35. The electrolocation apparatus of claim 34, wherein the high current pulses are greater than or equal to about 0.5 mA.

36. The electrolocation apparatus of claim 33, wherein the pulses are of the same duration and generated at approximately uniform intervals.

37. The electrolocation apparatus of claim 36, wherein the duration of the pulses is between about 0.1 to 0.2 milliseconds and the pulse intervals are between about 0.25 to 2.0 seconds.

38. A method of locating a nerve comprising the steps of:
providing an electrically conducting needle cannula having a proximal end, a distal end and a hollow bore therethrough;
inserting the needle into a patient and towards the nerve; and
alternatively generating charge pulses of electrical energy alternating between high and low charge pulses for stimulating the nerve and generating muscle twitches.

39. The method of claim 38, wherein the alternating charge pulses are generated by varying the time duration of the charge pulses.

40. The method of claim 39, wherein the time duration of the low charge pulse is between about 95 to 150 microseconds.

41. The method of claim 40, wherein the time duration of the high charge pulse is between about 375 to 600 microseconds.

42. The method of claim 38, wherein the alternating charge pulses are generated by varying the current level of the charge pulses.

43. The method of claim 42, wherein the time duration of the charge pulses is approximately the same duration.

44. The method of claim 43, wherein the low current pulses are less than or equal to about 0.2 mA.

45. The method of claim 44, wherein the high current pulses are greater than or equal to about 0.5 mA.

46. The method of claim 45, wherein the pulses are of the same duration and generated at approximately uniform intervals.

47. The method of claim 46, wherein the duration of the pulses is between about 0.1 to 0.2 milliseconds and the pulse intervals is between about 0.25 to 2.0 seconds.

48. The method of claim 38, further comprising the step of moving needle towards a targeted nerve wherein the muscle twitches elicited by the alternating charges become substantially indistinguishable.

* * * * *